United States Patent [19]
Haber et al.

[11] Patent Number: 5,122,118
[45] Date of Patent: Jun. 16, 1992

[54] AUTOMATIC NEEDLE-RETRACTING SYRINGE

[75] Inventors: Terry M. Haber, Lake Forest; Clark B. Foster, Laguna Niguel; William H. Smedley, Lake Elsinore, all of Calif.

[73] Assignee: Habley Medical Technology Corporation, Laguna Hills, Calif.

[21] Appl. No.: 533,134

[22] Filed: Jun. 1, 1990

[30] Foreign Application Priority Data

May 25, 1990 [IT] Italy .................... 21253/90[U]

[51] Int. Cl.$^5$ ................................ A61M 5/00
[52] U.S. Cl. ..................... 604/110; 604/198; 604/218; 604/221; 128/919
[58] Field of Search ............. 604/110, 111, 194–198, 604/187, 221, 263, 218, 222; 128/919

[56] References Cited

U.S. PATENT DOCUMENTS

| 2,771,880 | 11/1956 | Gotthart | 604/221 |
|---|---|---|---|
| 4,921,486 | 5/1990 | DeChellis et al. | 604/110 |
| 4,927,414 | 5/1990 | Kulli | 604/110 |
| 4,955,868 | 9/1990 | Klein | 604/198 |
| 4,966,593 | 10/1990 | Lennox | 604/198 |
| 4,973,316 | 11/1990 | Dysarz | 604/195 |
| 4,976,693 | 12/1990 | Haast | 604/110 |
| 4,994,034 | 2/1991 | Botich et al. | 604/110 |
| 5,017,187 | 5/1991 | Sullivan | 604/110 |
| 5,019,044 | 5/1991 | Tsao | 604/110 |
| 5,049,133 | 9/1991 | Villen Pascual | 604/110 |
| 5,053,010 | 10/1991 | McGary et al. | 604/110 |

FOREIGN PATENT DOCUMENTS

| 8801072 | 11/1989 | Netherlands | 604/263 |
|---|---|---|---|
| 1168260 | 6/1985 | U.S.S.R. | 604/187 |
| 89/00435 | 1/1989 | World Int. Prop. O. | 604/110 |
| 89/09075 | 10/1989 | World Int. Prop. O. | 604/195 |

Primary Examiner—C. Fred Rosenbaum
Assistant Examiner—M. Polutta
Attorney, Agent, or Firm—Townsend and Townsend

[57] ABSTRACT

An automatic needle-retracting syringe (2,80), intended for single use applications, includes a barrel (4), having a needle end (6), a plunger end (8) and a bore (10), and a plunger (12) at the plunger end. A needle gasket (16) is slidably mounted within the bore to define a near region (18) and a far region (20). A hollow needle (28) is mounted to the needle gasket. A path (26) through the needle gasket connects the near region to the needle. A coil spring (40,82) biases the needle gasket from an extended position to a retracted position, the needle fully housed within the barrel at the latter. The extended position is maintained by a retaining capsule (44) wedged between a narrowed bore portion (42) and the needle gasket. The retaining capsule is a gelatin which weakens upon contact with the liquid injectant so that after the liquid injectant contacts the retaining capsule for a period of time, the spring breaks the capsule causing the needle gasket to be moved back to the retracted position, thus retracting the needle back into the barrel. In addition, a supplemental flow path from the near region to the ambient environment can be created by dissolving a gelatin barrier to help prevent reuse of the syringe.

18 Claims, 3 Drawing Sheets

AUTOMATIC NEEDLE-RETRACTING SYRINGE

BACKGROUND OF THE INVENTION

The need to prevent re-use of syringes is widely recognized. One type of single-use syringe effectively destroys the barrel of the syringe through the use of tapered projections carried by the plunger which engage the walls of the syringe. Attempted withdrawal of the plunger from the syringe after an injection causes the tapered projections to puncture the walls. Another type of single-use syringe allows the needle to be retracted into the barrel for disposal. For example, see U.S. Pat. No. 4,507,117 to Vining, et al., dated Mar. 26, 1985 and U.S. Pat. No. 4,826,489 to Haber, et al., dated May 2, 1989.

One of the drawbacks of conventional single-use safety syringes is that they require the user to actively do something to make them safe. In some circumstances, such as when the syringe is being used by drug addicts, proper disposal procedures may not be used. This can result in inadvertent needle sticks by an unsuspecting person who happens to come in contact with the used syringe.

SUMMARY OF THE INVENTION

The present invention is directed to an automatic needle-retracting syringe in which the needle automatically retracts into the barrel of the syringe without the user doing anything. This typically occurs automatically after a predetermined time has lapsed from dispensing a liquid injectant from the syringe. Even if the used syringe is simply thrown onto the ground, the needle will automatically be retracted into the barrel after the period of time, such as 30 to 60 seconds after the injection.

The syringe includes a barrel having a needle end, a plunger end and a bore. A plunger is slidably mounted within the bore at the plunger end of the barrel. A needle gasket is slidably mounted within the bore to define a near region towards the plunger end and a far region towards the needle end.

A hollow needle having a base and a point is mounted to the needle gasket for movement with the needle gasket along the axis of the barrel. The base of the needle opens into a path formed within the needle gasket. The path opens into the near region of the bore.

A coil spring is positioned within the far region of the bore and biases the needle gasket away from the needle end of the barrel to a retracted position. When in the retracted position, the needle is fully housed within the barrel.

The needle gasket and needle therewith can be driven from the retracted position to an extended position in which the needle extends from the needle end of the barrel to permit the syringe to be used. The needle gasket and needle are preferably maintained in this extended position through the use of a retaining capsule. One part of the capsule is wedged into a narrowed portion of the bore adjacent the needle end of the barrel while another part engages the tip of the needle gasket. The strength of this engagement is strong enough to withstand the biasing force of the spring, which pushes the needle gasket towards the retracted position. The retaining capsule is made of a material which dissolves or otherwise weakens upon contact with the liquid injectant being used. Therefore, after a liquid injectant is drawn into the near region and is expulsed through the needle during use, the liquid injectant also contacts the retaining capsule, thus weakening the retaining capsule. After a period of time, the retaining capsule weakens to a point to permit the spring to break the capsule causing the needle gasket to be moved back to the retracted position, thus retracting the needle back into the barrel. In addition, breaking the retaining capsule prevents future injections by virtue of a supplemental flow path from the near region into the far region, the far region being open to the ambient environment.

The preferred embodiment, the retaining capsule serves a dual function of retaining the needle gasket in its extended position for a period of time, and also, after the retaining capsule has broken, of opening a supplemental pathway between the path passing through the needle gasket, through the far region and out a vent hole formed in the barrel wall and opening into the far region. Therefore, even if a user manages to keep the needle from automatically retracting, reuse can be prevented. These functions could, however, be provided by separate structures if desired.

A second supplemental path can be provided to selectively fluidly couple the near region to a supplemental region. The second supplemental path, in the preferred embodiment, is provided from the face of the plunger gasket through an axial bore in the plunger, the axial bore opening into the ambient environment. The far end of the plunger bore is sealed using a material which is dissolved or otherwise weakened by the liquid injectant after a period of time. Thus, after the liquid injectant touches the dissolvable barrier, the liquid injectant within the near region can flow through the plunger bore and, under appropriate conditions, into the ambient environment, rather than through the needle when the plunger is depressed.

Other features and advantages of the invention will appear from the following description in which the preferred embodiments have been set forth in detail in conjunction with the accompanying drawings.

DETAILED DESCRIPTION OF THE PREFERRED EMBODIMENTS

Figures 1, 2:
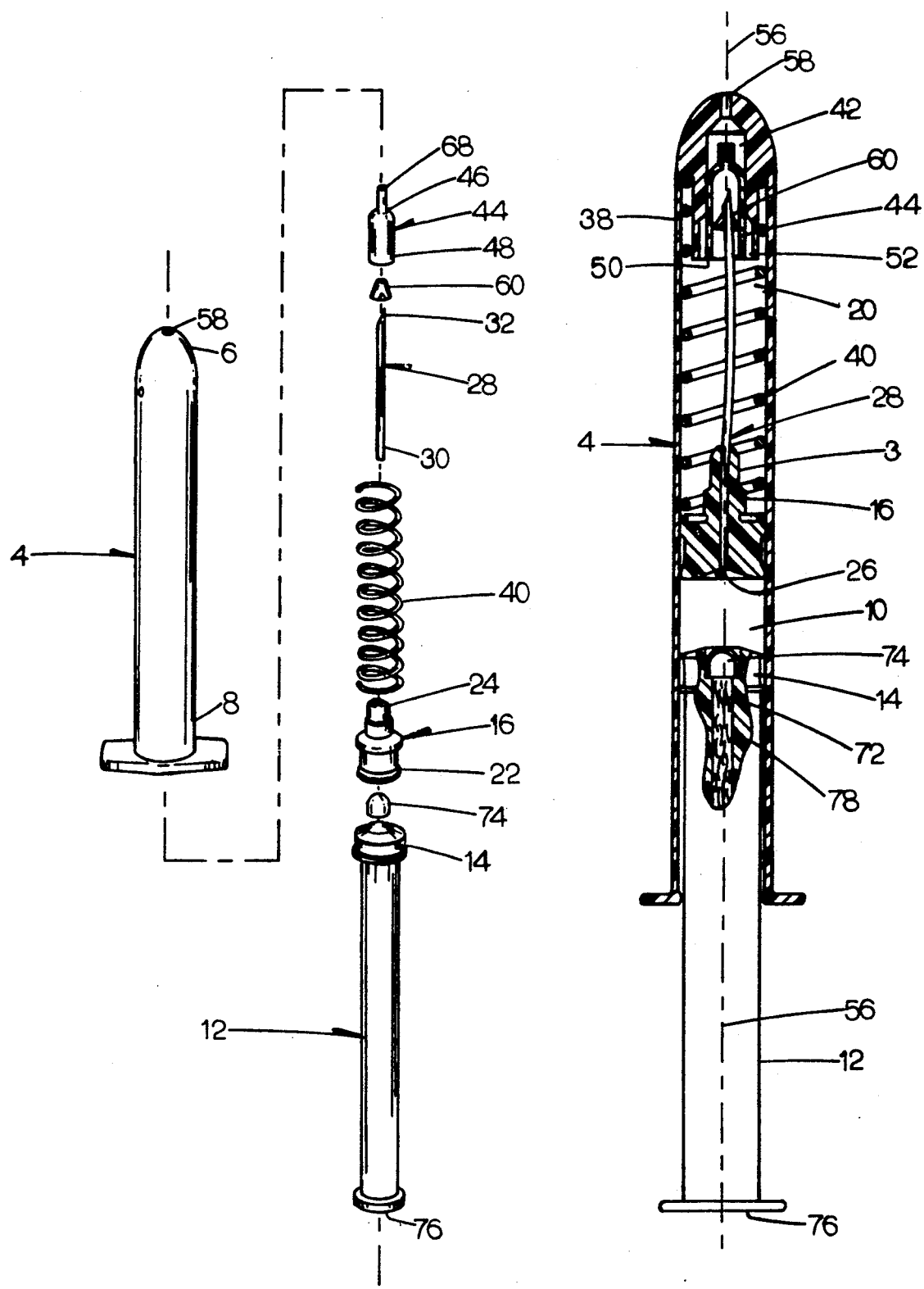
FIG. 1 is an exploded isometric view of an automatic needle retracting syringe made according to the invention.
FIG. 2 is a side cross-sectional view of the syringe of FIG. 1 shown in its assembled state with the needle gasket in its retracted position.

Syringe 2 as shown in FIGS. 1 and 2 includes a barrel 4 having a needle end 6 and a plunger end 8 and defining a bore 10 therein. A plunger 12, having a plunger gasket 14 at its far end, is mounted within bore 10 at plunger end 8. A movable needle gasket 16 is mounted within bore 10 to divide the bore into a near region 18 between needle gasket 16 and plunger end 8 and a far region 20 between needle gasket 16 and needle end 6.

Needle gasket 16 has a main body 22 and a tip 24. Main body 22 provides a sealing engagement with bore 10. Needle gasket 16 has a path 26 formed axially therein which opens into near region 18. A needle 28 having a base 30 and a point 32 is mounted to and carried by tip 24 of needle gasket 16. Base 30 of needle 28 connects to path 26 so that near region 18 is fluidly connected to point 32 of needle 28. Needle gasket 16 has a laterally extending hole 34 so that when needle gasket 16 and needle 28 therewith are in the retracted position of FIG. 2, a supplemental path is created from near region 18, along path 26, through hole 34, along far region 20 and through a vent hole 38 formed within barrel 4 near needle end 6. The usefulness of this supplemental path will become apparent when the operation of syringe 2 is discussed with reference to FIGS. 3-5.

Needle gasket 16 and needle 28 therewith are biased to the retracted position of FIG. 2 by a metal coil spring 40.

Bore 10 includes a narrowed bore portion 42 adjacent needle end 6 of barrel 4. A retaining capsule 44 is mounted within narrowed bore portion 42. The outer end 46 of retaining capsule 44 is wedged into narrowed bore portion 42 so retaining capsule 44 is quite securely affixed within narrowed bore portion 42. Instead of a frictional fit, retaining capsule 44 can be secured to a needle end 6 of barrel 4 and other ways, such as through the use of an adhesive. The inner end 48 of retaining capsule 44 extends into an intermediate bore portion 50 of far region 20. An annular gap 52 is defined between inner end 48 and intermediate bore portion 50.

Figures 3, 4, 5:
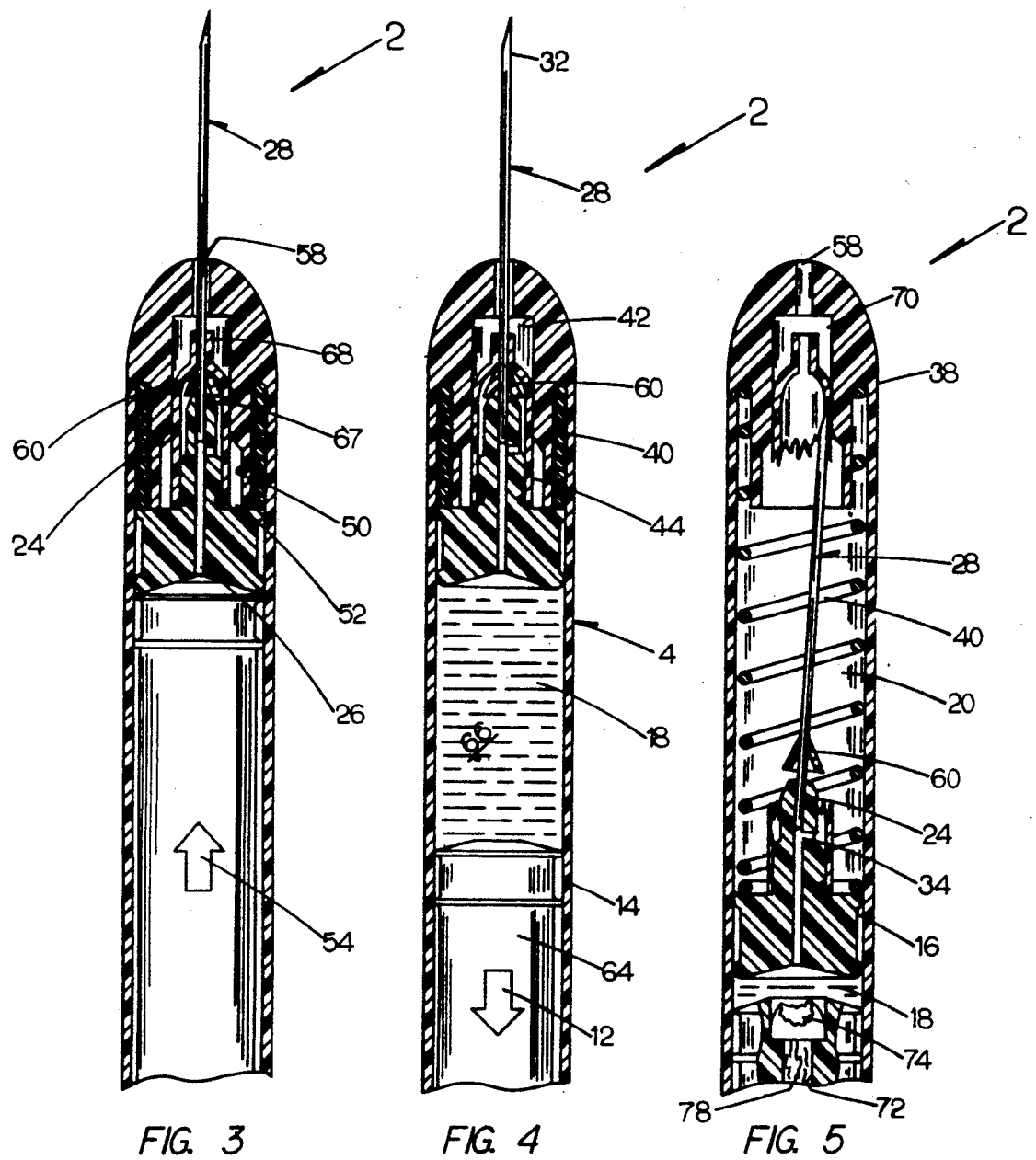
FIG. 3 is an enlarged partial side cross-sectional view of the syringe of FIG. 2 with the needle gasket in the extended position.
FIG. 4 illustrates the syringe of FIG. 3 with the needle gasket and needle in the extended position with a liquid injectant drawn into the near region of the bore.
FIG. 5 illustrates a syringe of FIG. 4 a period of time after a liquid injectant has been dispensed and the retaining capsule and dissolvable barrier have been broken due to the action of the liquid injectant weakening the retaining capsule and dissolvable barrier thus permitting the spring to drive the needle gasket and needle to the retracted position and preventing reuse of the syringe.

FIG. 3 illustrates syringe 2 with plunger 12 having been moved in the direction of arrow 54 thus forcing needle gasket 16 and needle 28 therewith from the retracted position of FIG. 2 to the extended position of FIG. 3 with needle 28 extending from needle end 6 of barrel 4. FIG. 3 also shows that spring 40 has been compressed and that tip 24 of needle gasket 16 has been forced into the interior of retaining capsule 44.

Tip 24 is configured to direct needle 28 in a direction offset to axis 56 of bore 10. This is done to prevent needle 28 from being driven outside of barrel 4 after use, as discussed below with reference to FIG. 5. However, to permit needle 28 to pass through opening 58 at needle end 6 of barrel 4, a needle guide 60 is mounted near point 32 of needle 28 as shown in FIG. 2. A slight bow in needle 28 is evident from FIG. 2.

Needle glide 60 has been moved from its position towards inner end 48 of retaining capsule 44 of FIG. 2 to outer end 46 of the retaining capsule of FIG. 3. Plunger 12 is moved in the direction of arrow 64 to draw a liquid injectant 66 into near region 18 of bore 10 as illustrated in FIG. 4. Movement of plunger 12 in the direction of arrow 54 forces liquid injectant 66 through path 26, hollow needle 28 and out point 32. Liquid injectant 66 is also forced through hole 34 and into the region 67 between tip 24 and the interior of capsule 4.

Retaining capsule 44 is made to dissolve or otherwise be weakened when subjected to injectant 66. Presently, a retaining capsule 44 made of water based dissolvable gelatin, such as used with medicinal capsules, having a wall thickness of about 0.008" to 0.010" (2.0 mm to 2.5 mm) and used with a water based liquid injectant 66, has proven satisfactory. After retaining capsule 44 has been sufficiently weakened, typically 30-60 seconds, spring 40 causes retaining capsule 44 to break as illustrated in FIG. 5 forcing needle gasket 16 back to the retracted position of FIG. 2. Further, the separation of inner end 48 from outer end 46 of retaining capsule 44 opens the supplemental path connecting near region 18 with the ambient environment through path 26, hole 34, region 18 and vent hole 38. Thus, subsequent attempted use would likely cause any liquid injectant within near region 18 to be forced through the supplemental path instead of through needle 28.

Needle guide 60 is driven into outer end 46 of retaining capsule 44 by the initial movement of needle gasket 16 and needle 28 from the retracted position of FIG. 2 to the extended position of FIG. 3. As needle 28 continues in the direction of arrow 54, needle guide 60 is driven along needle 28 until the needle guide rests against tip 24 of needle gasket 16. As shown in FIG. 5, needle guide 60 remains adjacent tip 24 when needle gasket 16 and needle 28 moves in the direction of arrow 64. This occurs because sufficient friction is created between needle guide 60 and needle 28. Since needle 28 is no longer constrained by needle guide 60, tip 24 of needle gasket 16 causes needle 28 to move sideways as shown in FIG. 5. Any attempt to drive needle 28 back through opening 58 is prevented by the engagement of point 32 with a shoulder 70 connecting narrow bore portion 42 and opening 58.

FIG. 5 also illustrates a plunger bore 72 formed along plunger 12. Plunger bore 72 is normally sealed by a dissolvable barrier 74 as shown in FIG. 2. After an appropriate period of time, such as 30-90 seconds, dissolvable barrier 74 will either disintegrate or break under the application of pressure to allow the passage of fluid from near region 18, through plunger bore 72 and out one or more lateral openings, not shown, formed in the plunger. Plunger bore 72 is filled with an absorbent material 78. Material 78 helps keep any leftover liquid injectant 66 from leaking from syringe 2 after use. Further, providing a second supplemental path from region 18, along bore 72 into the ambient environment helps insure that syringe 2 will not be re-used even if one were to keep needle 28 from automatically retracting, such as by wedging something into opening 58 while needle 28 is in the extended position. The breaking of barrier 74 prevents creation of a positive or a negative pressure in near region 18. Another way to prevent the creation of a positive or a negative pressure within near region 18 would be to make the sealing surfaces of plunger gasket 14 from a material which dissolves or is otherwise softened by a liquid injectant so the sealing effectiveness of plunger gasket 14 is destroyed after a period of time from contact with the liquid injectant.

Figure 6:
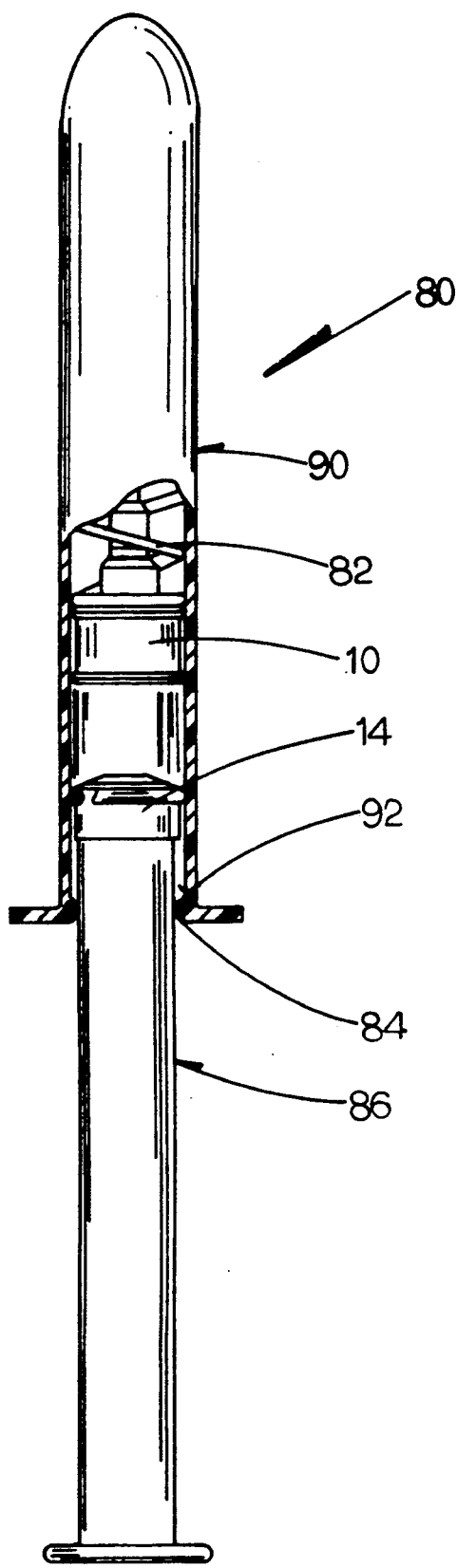
FIG. 6 is a side elevational view of an alternative embodiment of the syringe of FIG. 2 with a portion of the barrel broken away and shown in the retracted position.
Figure 7:
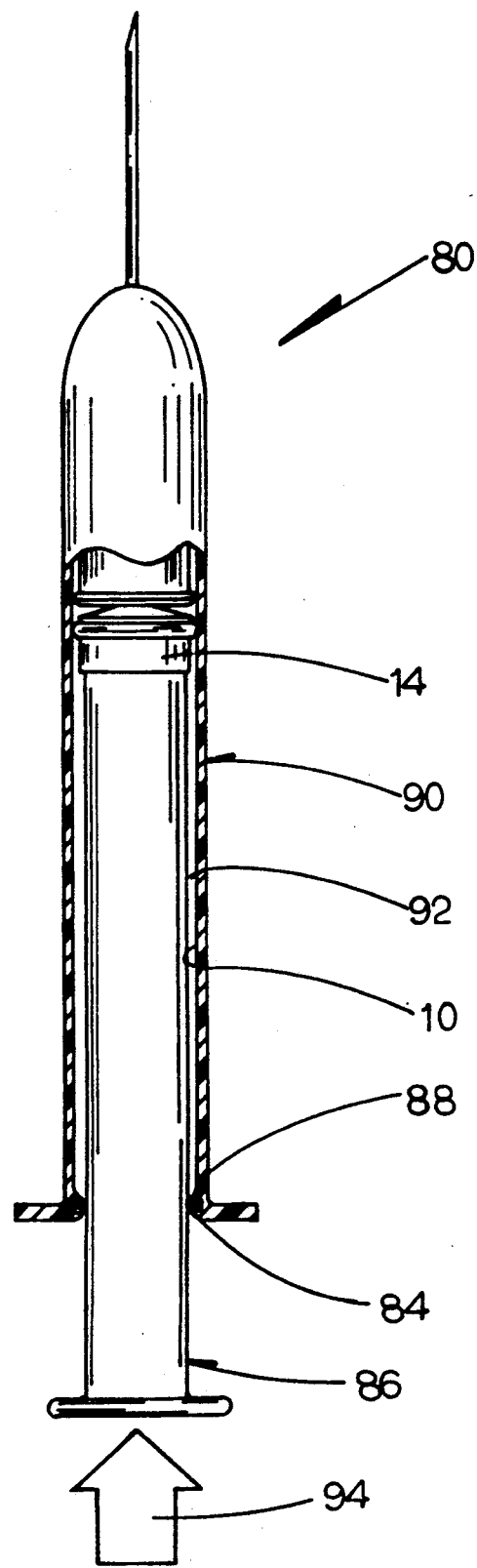
FIG. 7 illustrates the syringe of FIG. 6 in the extended position.

An alternative embodiment of invention is shown in FIGS. 6 and 7. Syringe 80 is similar to syringe 2 that includes a plastic spring 82 in lieu of the metal coil spring 40 of syringe 2. Because the force expected to be generated by spring 82 will be less than available with metal spring 40, syringe 80 has been designed to help spring 82 move needle gasket 16 and needle 28 therewith from the extended position of FIG. 7 to the retracted position of FIG. 6. This is accomplished by providing a supplemental seal 84 between plunger 86 and the plunger end 88 of barrel 90. When the user drives plunger 86 from the position of FIG. 6 to the position of FIG. 7 while dispensing a liquid injectant, a partial vacuum is formed and space 92 between bore 10 and plunger 86 from plunger gasket 14 to supplemental seal 84. The partial vacuum tends to draw plunger 86 out of barrel 90 in the direction opposite arrow 94. This helps spring 82 from having to push plunger 86 while it also breaks capsule 44. The diameter of plunger 86 may be adjusted to provide a different volume for space 92.

The present invention has been shown with retaining capsule 44 initially mounted within narrowed bore portion 42. Capsule 44 could also be initially mounted to tip 24 of needle gasket 16 and driven into engagement with narrowed bore portion 42. Also, the invention could be used as a pre-filled syringe. One way to do so would be to place needle gasket 16 and needle 28 therewith in the extended position of FIG. 3, along with a sheath covering the needle, and a supply of the liquid injectant between needle gasket 16 and plunger gasket 14. A thin membrane could be stretched across the face of needle gasket 16 encasing near region 18 to keep a liquid injectant from entering path 26. However, pressing on plunger 12 would cause the membrane to deflect towards the conical surface of needle gasket 16. The conical surface would be provided with several sharp projections which would pierce the deflected membrane permitting the injection to be made. Also, the supplemental path feature could be used with conventional syringes as well.

Other modifications with variations can be made to disclose embodiments without departing from the subject of the invention as defined in the following claims. For example, the invention could be used with a pump and an IV drip. In this situation a supplemental needle, connected to a low flow rate pump, is used to slowly inject a medicine into the IV line through a port. After a certain period of time, such as 2 hours, the medicine could become toxic or simply inert. The invention could be used to automatically withdraw the supplemental needle from the port so to prevent additional medicine from being introduced into the IV line.

What is claimed is:

1. An automatic needle retracting syringe for use with a liquid injectant comprising:
    a barrel having a needle end, a plunger end and defining a bore therein;
    a plunger slidably mounted within the bore at the plunger end;
    a needle gasket slidably mounted within the bore to divide said bore into a near region towards the plunger end and a far region towards the needle end, the needle gasket having a path formed therein communicating with the near region;
    a hollow needle having a base and a point, the base mounted to the needle gasket in fluid communication with the path;
    means for biasing the needle gasket and needle therewith towards a retracted position, the needle being housed entirely within the far region when the needle gasket is at the retracted position;
    the needle gasket being movable between the retracted position and an extended position at which the tip of the needle extends from the needle end; and
    means for maintaining the needle gasket in the extended position, said maintaining means including a dissolvable portion wedgeable between the tip of the needle gasket and the needle end of the barrel, the dissolvable portion configured to retain the tip of the needle gasket near the needle end of the barrel when the needle gasket is in the extended position, the dissolvable portion weakening upon contact with the liquid injectant over a period of time so as to release the needle gasket and permit the biasing means to move the needle gasket and needle therewith to the retracted position.

2. The syringe of claim 1 wherein the dissolvable portion of the maintaining means is positioned to come into contact with the liquid injectant when the liquid injectant is delivered through the needle.

3. The syringe of claim 1 further comprising a supplemental pathway fluidly coupling the near region with the ambient environment without passing through the needle, said supplemental pathway being sealed by the maintaining means prior to the dissolvable portion releasing the needle gasket, said supplemental pathway being opened by the maintaining means after the dissolvable portion has released the needle gasket.

4. The syringe of claim 1 wherein the dissolvable portion is configured as a cup-like capsule.

5. The syringe of claim 4 wherein the needle gasket includes a tip from which the needle extends, the capsule has an inner end and an outer end and the tip is sized to fit within the inner end of the capsule, the outer end sized to fit within a narrowed portion of the bore, the fits between the tip and the inner end of the capsule and between the narrowed bore portion and the outer end of the capsule being tight fits so to retain the tip in the capsule and retain the capsule in narrowed portion of the bore and thereby secure the needle gasket in the extended position.

6. The syringe of claim 5 wherein the path passes through the tip and further comprising a supplemental path connecting the path to a region between the tip and an inside surface of the capsule to permit the liquid injectants to contact the capsule during use of the syringe thereby weakening the capsule sufficiently after the period of time to permit the biasing means to break the capsule and move the needle gasket towards the retracted position.

7. The syringe of claim 1 further comprising:
    a supplemental pathway fluidly coupling the near region to a supplemental region; and
    means for sealing the supplemental pathway until the passage of a second period of time after the liquid injectant has been drawn into the near region.

8. The syringe of claim 7 wherein the supplemental pathway includes a plunger bore formed within the plunger.

9. The syringe of claim 8 wherein the supplemental region includes the ambient environment.

10. The syringe of claim 7 further comprising a liquid absorbent material within at least a portion of the supplemental region.

11. The syringe of claim 1 further comprising means for preventing movement of the needle gasket and needle therewith to the extended position after the biasing means has moved the needle gasket and needle therewith to the retracted position.

12. The syringe of claim 11 wherein the movement preventing means include means for laterally biasing the needle away from coaxial alignment with the bore of the barrel.

13. The syringe of claim 1 wherein the biasing means includes a metal coil spring.

14. The syringe of claim 1 wherein the biasing means include a plastic spring.

15. A single use syringe for use with a liquid injectant comprising:
   a barrel having a needle end, a plunger end and defining a bore therein;
   a plunger slidably mounted within the bore at the plunger end, the plunger including a plunger gasket defining an injectant region between the plunger gasket and the needle end of the barrel;
   a hollow needle extending from the needle end of the barrel and having a point and a base, the base in fluid communication with the injectant region;
   a supplemental pathway fluidly coupling the injectant region and a supplemental region the supplemental region includes an axial bore within the plunger; and
   means for sealing the supplemental pathway until a period of time after the liquid injectant has been in contact with the sealing means, said sealing means being weakened by said contact with the liquid injectant so to permit flow of the liquid injectant from the injection region to the supplemental region after the period of time.

16. The syringe of claim 15 wherein the sealing means include a barrier made of a water soluble gelatin material.

17. The syringe of claim 15 wherein the supplemental region includes the ambient environment.

18. An automatic needle retracting syringe for use with a liquid injectant comprising:
   a barrel having a needle end, a plunger end and defining a bore therein;
   a plunger slidable mounted within the bore and extending out from the bore at the plunger end;
   a hollow needle having a base and a point and mounted to a needle gasket, the needle gasket slidably mounted within the bore to divide said bore into a near region towards the plunger end and a far region towards the needle end, the needle gasket having a main body, a tip extending towards the far region, a path fluidly coupling the point to the near region and a hole fluidly coupling the path to the far region;
   a spring disposed within the barrel between the needle gasket and the needle end, the spring biasing the needle gasket and needle therewith towards a retracted position wherein in the retracted position the needle is housed entirely within the barrel;
   the needle gasket being movable between the retracted position and an extended position at which the point of the needle extends from the needle end of the barrel;
   a dissolvable capsule secured in the barrel near the needle end and configured to receive and frictionally retain the tip of the needle gasket when the needle gasket is in the extended position, the dissolvable capsule constructed of material which dissolves upon contact with the liquid injectant over a period of time so as to compromise the frictional engagement between the tip and the capsule and thereby permit the spring to move the needle gasket and needle therewith to the retracted position;
   an axial bore within the plunger fluidly coupled to the near region;
   a dissolvable sealing means disposed within said axial bore which weakens during contact with the liquid injectant so to permit flow of the liquid injectant from the near region through axial bore and into a supplemental region.

* * * * *